United States Patent [19]

Leyendecker et al.

[11] Patent Number: 5,180,727

[45] Date of Patent: Jan. 19, 1993

[54] PHENOXYALKYL-SUBSTITUTED HETEROAROMATICS AND THEIR USE FOR CONTROLLING PESTS

[75] Inventors: Joachim Leyendecker, Ladenburg; Hans-Juergen Neubauer, Muenster-Hiltrup; Uwe Kardorff, Mannheim; Christoph Kuenast, Otterstadt; Peter Hofmeister, Neustadt; Wolfgang Krieg, Weingarten, all of Fed. Rep. of Germany

[73] Assignee: BASF Aktiengesellschaft, Ludwigshafen, Fed. Rep. of Germany

[21] Appl. No.: 834,839

[22] Filed: Feb. 13, 1992

Related U.S. Application Data

[62] Division of Ser. No. 606,813, Oct. 31, 1990, Pat. No. 5,132,308, which is a division of Ser. No. 389,815, Aug. 4, 1989, Pat. No. 4,996,216.

[30] Foreign Application Priority Data

Aug. 5, 1988 [DE] Fed. Rep. of Germany ....... 3826681
Aug. 5, 1988 [DE] Fed. Rep. of Germany ....... 3826682

[51] Int. Cl.$^5$ ............... A01N 43/60; C07D 417/12; C07D 413/12; C07D 403/12
[52] U.S. Cl. ................................. 514/255; 544/405
[58] Field of Search ................... 544/405; 514/255

[56] References Cited

U.S. PATENT DOCUMENTS 4,943,585 7/1990 Buerstinghaus et al. ........... 514/398

*Primary Examiner*—Patricia L. Morris
*Attorney, Agent, or Firm*—Oblon, Spivak, McClelland, Maier & Neustadt

[57] ABSTRACT

Phenoxyalkyl-substituted heteroaromatics of the general formulae Ia and Ib

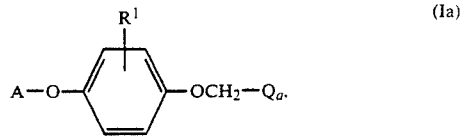

(Ia)

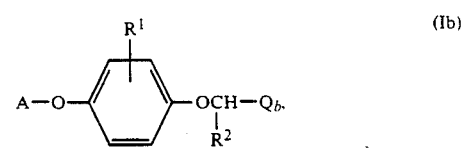

(Ib)

where A is an unsubstituted or substituted heteroaromatic radical having 6 ring members and 1, 2 or 3 nitrogen atoms in the ring, $R^1$ is hydrogen, halogen or $C_1$-$C_3$-alkyl, $R^2$ is hydrogen or $C_1$-$C_4$-alkyl, $Q_a$ is an unsubstituted or substituted azole radical and $Q_b$ is a substituted or unsubstituted heteroaromatic radical which has a five-menbered ring, and their use for combating pests.

6 Claims, No Drawings

PHENOXYALKYL-SUBSTITUTED HETEROAROMATICS AND THEIR USE FOR CONTROLLING PESTS

This is a division of application Ser. No. 07/606,813, filed on Oct. 31, 1990, now U.S. Pat. No. 5,132,308 which is a division of application Ser. No. 07/389,815, filed Aug. 4, 1989, now U.S. Pat. No. 4,996,216.

The present invention relates to novel phenoxyalkyl-substituted heteroaromatics of the general formulae Ia and Ib

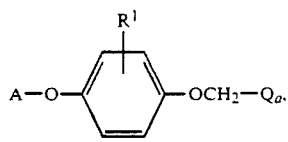

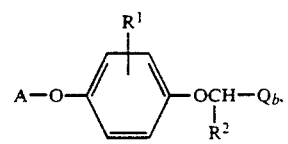

where A is an unsubstituted or substituted heteroaromatic radical having 6 ring members and 1, 2 or 3 nitrogen atoms in the ring, $R^1$ is hydrogen, halogen or $C_1$–$C_3$-alkyl, $R^2$ is hydrogen or $C_1$–$C_4$-alkyl, $Q_a$ is an unsubstituted or substituted azole radical of the formulae IIa to IIe

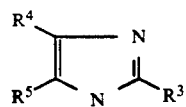

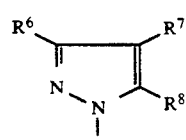

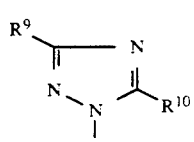

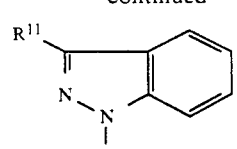

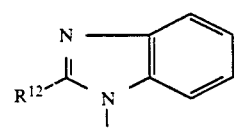

$R^3$ to $R^{12}$ are each hydrogen, halogen $C_1$–$C_8$-alkyl, $C_1$–$C_4$-haloalkyl, $C_1$–$C_4$-alkoxy, $C_3$–$C_{10}$-cycloalkyl or aryl which is unsubstituted or monosubstituted to trisubstituted by halogen, $C_1$–$C_8$-alkyl, $C_1$–$C_8$-alkoxy, $C_1$–$C_4$-haloalkyl or $C_1$–$C_3$-haloalkoxy, and $Q_b$ is a heteroaromatic radical which has a five-membered ring, is bonded via a carbon atom and is unsubstituted or monosubstituted or polysubstituted by halogen, $C_1$–$C_8$-alkyl, $C_2$–$C_8$-alkenyl, $C_1$–$C_4$-haloalkyl, $C_1$–$C_8$-alkoxy, $C_1$–$C_8$-alkylthio, $C_2$–$C_8$-alkoxyalkyl or $C_3$–$C_{10}$-cycloalkyl, with the proviso that $R^2$ is not methyl when $Q_b$ is alkoxy-substituted 1,3,4-thiazol-2-yl and A is simultaneously substituted pyrid-2-yl.

The present invention furthermore relates to pesticides which contain the compounds Ia or Ib as active ingredients, and a method for controlling pests.

Japanese Patent Application JP 55/28923 describes N-substituted azoles as fungicidal active ingredients. Furthermore, EP-A-132 606 discloses N-substituted azoles as insecticidal and acaricidal active ingredients, although their action is unsatisfactory, particularly at low application rates.

EP-A-92706, DE-A-3 408 528 and Japanese Applications JP 57/175177, JP 57/175179 and JP 59/98083 describe phenoxyalkyl-substituted heteroaromatics as herbicidal active ingredients; these publications make no reference to insecticidal action.

It is an object of the present invention to provide novel phenoxyalkyl-substituted heteroaromatics having an improved action.

We have found that this object is achieved by the novel phenoxyalkyl-substituted heteroaromatics defined at the outset. We have also found that the compounds Ia and Ib are very suitable for controlling pests.

The compounds Ia and Ib are obtainable by the following method:

A phenol III and an N-methylazole IVa or a heteroaromatic IVb having a five-membered ring are reacted in the presence of a base at from $-20°$ to $250°$ C., preferably from $20°$ to $120°$ C., in accordance with the following equation:

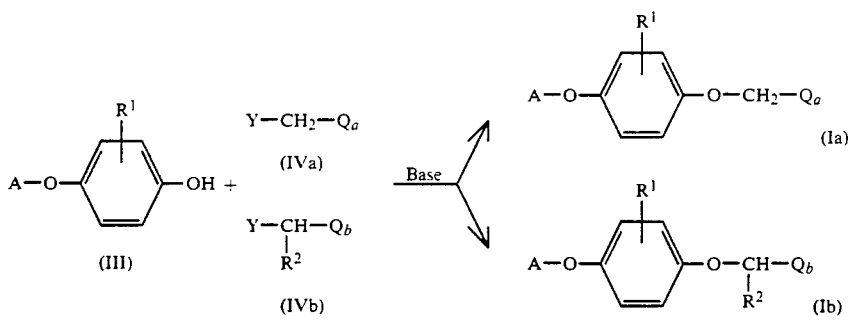

Instead of the phenol III plus the base, it is also possible to react the phenolate ion of III directly with IVa or IVb. In this case, the reaction temperatures are preferably from −20° to 120° C., in particular from −20° to 80° C.

In the above equations, Y is a conventional leaving group, for example a sulfonyl radical or a halogen. Among the sulfonyl radicals, methanesulfonyl, trifluoromethanesulfonyl and p-toluenesulfonyl are preferred, while preferred halogens are chlorine and bromine; chlorine is particularly preferred.

Some of the phenols III are disclosed in CH-A-652 714, Res. Discl. 214 (1982), 32 and DE-A-33 20 534, or can be prepared by the methods described there.

Some of the N-methylazoles IVa are disclosed in Heterocycles 24 (1986), 2233-2237 or can be prepared by the method described there, in accordance with the following equation:

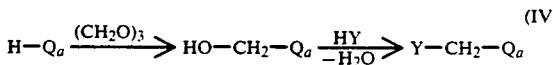

(IVa)

Either the heteroaromatics IVb are known and some of them are commercially available, or they can be prepared by generally known chemical processes. Processes for the preparation of thiophene derivatives are described in, for example, Comprehensive Heterocyclic Chemistry, A. R. Katritzky and C. W. Rees, Vol. 4, page 863 et seq., Pergamon Press 1984, those for the preparation of furan derivatives are described in, for example, DE-A-3 514 384, DE-A-3 546 371 or Advances in Heterocyclic Chemistry 30 (1982), 167 et seq., those for the preparation of pyrrole derivatives are described in, for example, Comprehensive Heterocyclic Chemistry, A. R. Katritzky and C. W. Rees, Vol. 4, page 313 et seq., Pergamon Press, 1984, those for the preparation of thiazole derivatives, oxazole derivatives, isothiazole derivatives, thiadiazole derivatives and oxadiazole derivatives are described in, for example, Comprehensive Heterocyclic Chemistry, A. R. Katritzky and C. W. Rees, Vol. 6, pages 235, 177, 131, 447, 365 et seq., Pergamon Press, 1984, those for the preparation of imidazole derivatives are described in, for example, Advances in Heterocyclic Chemistry 27 (1980), 242 et seq., those for the preparation of pyrazole derivatives are described in, for example, Heteroaromatic Nitrogen Compounds, The Azoles, page 31 et seq., Cambridge University Press, 1976, those for the preparation of thiazole derivatives are described in, for example, Comprehensive Heterocyclic Chemistry, A. R. Katritzky and C. W. Rees, Vol. 5, page 669 et seq., Pergamon Press, 1984, and those for the preparation of isoxazole derivatives are described in, for example, DE-A-2 549 962 and DE-A-2 754 832.

Usually, not less than equivalent amounts of a base, based on III, are added to III and/or IVa or IVb, but the base may also be used in excess or, if required, also as a solvent.

Examples of suitable bases are hydroxides of alkali metals and alkaline earth metals, such as sodium hydroxide, potassium hydroxide and calcium hydroxide, alcoholates of alkali metals and alkaline earth metals, such as sodium methylate, sodium ethylate, calcium methylate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, aromatic amines, such as pyridine or pyrrole, and, if required, also alkyllithium compounds, such as n-butyllithium.

The reaction is advantageously carried out in a solvent or diluent. Examples of suitable solvents and diluent are aliphatic hydrocarbons, such as n-pentane, n-hexane, the hexane isomer mixture and petroleum ether, aromatic hydrocarbons, such as benzene, toluene, xylenes and their isomer mixtures and gasoline, alcohols, such as methanol, ethanol, n-propanol and isopropanol, ethers, such as diethyl ether, di-n-butyl ether, methyl tert-butyl ether, tetrahydrofuran and dioxane, ketones, such as acetone, methyl ethyl ketone and methyl isopropyl ketone, nitriles, such as acetonitrile and propionitrile, and aprotic dipolar solvents, such as dimethylformamide, dimethyl sulfoxide or pyridine. Mixtures of these substances may also be used as solvents and diluents.

For the preparation of the novel compounds I by the method described above, the starting materials are usually used in a stoichiometric ratio. An excess of one or other of the starting materials may, however, be quite advantageous in specific cases.

The reactions usually take place at sufficient rates at above −20° C. In general, it is not necessary to exceed 120° C. Since some of the reactions take place with evolution of heat, it may be advantageous to provide a means of cooling.

The reaction mixtures are worked up in a conventional manner, for example by the addition of water, separation of the phases and column chromatography. Some of the novel compounds of the formula I are obtained in the form of colorless or pale brown, viscous oils, which can be freed from the final volatile constituents by prolonged heating under reduced pressure at moderately elevated temperatures (incipient distillation) and can be purified in this manner. If the compounds of the formula Ia or Ib are obtained in crystalline form, they can be purified by recrystallization.

The substituents in formula I have the following specific meanings:

A is an unsubstituted or substituted heteroaromatic radical having 6 ring members and 1, 2 or 3 nitrogen atoms in the ring, for example of the formulae Va to Ve

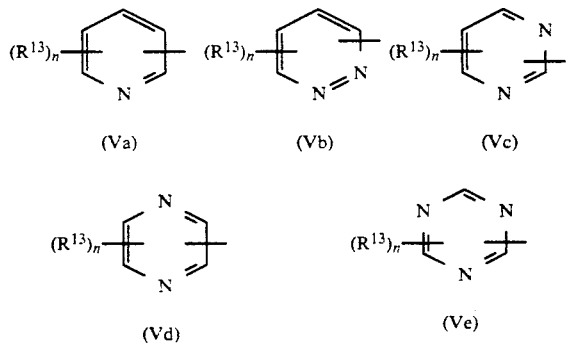

where the radicals $R^{13}$ are identical or different and are each hydrogen, halogen, $C_1$-$C_4$-alkyl, $C_1$-$C_3$-haloalkyl, $C_1$-$C_4$-alkoxy, $C_1$-$C_3$-haloalkoxy, $C_3$-$C_6$-cycloalkyl, cyano or nitro and n is from 1 to 4, preferred heteroaromatic radicals being pyrid-2-yl, pyrid-3-yl, pyrid-4-yl, pyrimidin-2-yl, pyrimidin-4-yl, pyrimidin-5-yl, pyridazin-3-yl, pyridazin-4-yl, pyrazin-2-yl, pyrazin-3-yl and 1,3,5-triazin-2-yl, in particular pyrid-2-yl, pyrimidin-2-yl, pyrimidin-4-yl, pyrimidin-5-yl, pyridazin-3-yl and pyrazin-2-yl and suitable radicals $R^{13}$ being, independently of one another, hydrogen, halogen, such as fluorine, chlorine or bromine, in particular fluorine or chlorine, straight-chain or branched $C_1$-$C_4$-alkyl, such as methyl, ethyl, propyl, butyl, in particular straight-chain alkyl, such as methyl or ethyl, or branched alkyl, such as isopropyl, isobutyl or sec-butyl, straight-chain or branched $C_1$-$C_3$-haloalkyl, in particular fluoro- or chloroalkyl, such as fluoromethyl, difluoromethyl, trifluoromethyl, pentafluoroethyl, 2,2,2-trifluoroethyl, chloromethyl, dichloromethyl, trichloromethyl or 2,2,2-trichloroethyl, straight-chain or branched $C_1$-$C_4$-alkoxy, in particular methoxy, ethoxy or isopropoxy, straight-chain or branched $C_1$-$C_3$-haloalkoxy, in particular fluoro- or chloroalkoxy, such as trifluoromethoxy, trichloromethoxy, 1,1,2,2-tetrafluoroethoxy or pentafluoroethoxy, $C_3$-$C_6$-cycloalkyl, such as cyclopropyl, cyclobutyl, cyclopentyl or cyclohexyl, in particular cyclopropyl, cyano or nitro, $R^1$ is hydrogen, halogen, such as fluorine, chlorine or bromine, preferably fluorine or chlorine, straight-chain or branched $C_1$-$C_3$-alkyl, such as methyl, ethyl, propyl or isopropyl, $R^2$ is hydrogen, $C_1$-$C_4$-alkyl, such as methyl, ethyl, propyl, isopropyl or butyl, particularly preferably methyl, $R^3$ to $R^{12}$ independently of one another are each hydrogen, halogen, preferably fluorine or chlorine, straight-chain or branched $C_1$-$C_8$-alkyl, preferably straight-chain or branched $C_1$-$C_4$-alkyl, such as methyl, ethyl, propyl or butyl, particularly preferably $C_1$- or $C_2$-alkyl, such as methyl or ethyl, straight-chain or branched $C_1$-$C_4$-haloalkyl, preferably $C_1$- or $C_2$-fluoro- or chloroalkyl, particularly preferably trifluoromethyl or trichloromethyl, straight-chain or branched $C_1$-$C_8$-alkoxy, preferably straight-chain or branched $C_1$-$C_4$-alkoxy, particularly preferably $C_1$- or $C_2$-alkoxy, such as methoxy or ethoxy, $C_3$-$C_{10}$-cycloalkyl, preferably $C_3$-$C_6$-cycloalkyl, such as cyclopropyl, cyclobutyl, cyclopentyl or cyclohexyl, particularly preferably cyclopropyl, aryl, preferably phenyl, 1-naphthyl or 2-naphthyl, particularly preferably phenyl, aryl which is monosubstituted to trisubstituted by halogen, preferably phenyl which is monosubstituted by fluorine or chlorine, such as 2-fluorophenyl, 3-fluorophenyl, 4-fluorophenyl, 2-chlorophenyl, 3-chlorophenyl or 4-chlorophenyl, aryl which is monosubstituted to trisubstituted by straight-chain or branched $C_1$-$C_8$-alkyl, preferably phenyl which is monosubstituted by straight-chain or branched $C_1$-$C_4$-alkyl, particularly preferably phenyl which is monosubstituted by $C_1$- or $C_2$-alkyl, such as 4-methylphenyl or 4-ethylphenyl, aryl which is monosubstituted to trisubstituted by straight-chain or branched $C_1$-$C_8$-alkoxy, preferably phenyl which is monosubstituted by straight-chain or branched $C_1$-$C_4$-alkoxy, particularly preferably phenyl which is monosubstituted by $C_1$- or $C_2$-alkoxy, such as 4-methoxyphenyl or 4-ethoxyphenyl, or aryl which is monosubstituted to trisubstituted by straight-chain or branched $C_1$-$C_4$-haloalkoxy, preferably phenyl which is monosubstituted by $C_1$- or $C_2$-fluoro- or chloroalkoxy, particularly preferably phenyl which is monosubstituted by trifluoromethoxy or trichloromethoxy, such as 4-trifluoromethoxyphenyl or 4-trichloromethoxyphenyl, and $Q_b$ is an unsubstituted or substituted heteroaromatic radical which has a five-membered ring and 1 to 4, in particular 1, 2 or 3, heteroatoms, such as nitrogen, sulfur or oxygen, preferably unsubstituted or substituted thiophen-2-yl, thiophen-3-yl, thiazol-2-yl, thiazol-4-yl, thiazol-5-yl, oxazol-2-yl, oxazol-4-yl, oxazol-5-yl, imidazol-2-yl, imidazol-4-yl, imidazol-5-yl, isothiazol-3-yl, isothiazol-4-yl, isothiazol-5-yl, pyrazol-3-yl, pyrazol-4-yl, isoxazol-3-yl, isoxazol-5-yl, 1,3,4-thiadiazol-2-yl, 1,3,4-oxadiazol-2-yl, 1,2,4-oxadiazol-3-yl, 1,3,4-triazol-2-yl or 1,2,4-thiadiazol-3-yl, particularly preferably thiophen-2-yl, thiophen-3-yl, thiazol-4, imidazol-5-yl, 1,3,4-thiadiazol-2-yl, 1,3,4-oxadiazol-2'-yl, 1,2,4-oxadiazol-3-yl, isoxazol-3-yl or isoxazol-5-yl.

The heteroaromatic radical having a five-membered ring may be unsubstituted or monosubstituted or polysubstituted by:

halogen, preferably fluorine, chlorine or bromine, particularly preferably chlorine or bromine, $C_1$-$C_8$-alkyl, preferably $C_1$-$C_4$-alkyl, particularly preferably methyl, ethyl, isopropyl or tert-butyl, $C_2$-$C_8$-alkenyl, preferably $C_2$-$C_4$-alkenyl, particularly preferably ethenyl, 1-methylethen-1-yl, propen-1-yl or 2-methylpropen-1-yl, $C_1$-$C_4$-haloalkyl, preferably fluorine-substituted or chlorine-substituted $C_1$- or $C_2$-haloalkyl, particularly preferably trifluoromethyl or 2,2,2-trifluoroethyl, $C_1$-$C_8$-alkoxy, preferably $C_1$-$C_3$-alkoxy, particularly preferably methoxy, ethoxy, n-propoxy or isopropoxy, $C_1$-$C_8$-alkylthio, preferably $C_1$-$C_3$-alkylthio, particularly preferably methylthio, ethylthio, n-propylthio or isopropylthio, $C_2$-$C_8$-alkoxyalkyl, preferably $C_2$-$C_4$-alkoxyalkyl, particularly preferably methoxymethyl, 1-methoxyethyl, 2-methoxyethyl or 1-methoxypropyl, or $C_3$-$C_8$-cycloalkyl, preferably $C_3$-$C_5$-cycloalkyl, particularly preferably cyclopropyl, cyclobutyl or cyclopentyl.

The phenoxyalkyl-substituted heteroaromatics of the general formula Ia or Ib are suitable for effectively controlling pests from the class consisting of the insects, arachnids and nematodes. They can be used as pesticides in crop protection, in the hygiene and veterinary sectors and for the protection of stored materials.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

Examples of formulations are given below.

I. 5 parts by weight of compound no. 1.2 is intimately mixed with 95 parts by weight of particulate kaolin. A dust is obtained containing 5% by weight of the active ingredient.

II. 30 parts by weight of compound no. 1.2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 1.13 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 6.3 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 6.22 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.001 to 10, particularly from 0.1 to 2, and preferably from 0.01 to 1, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

MANUFACTURING EXAMPLES

EXAMPLE 1

1-[4-(6-Chloro-2-pyridinyloxy)-phenoxymethyl]-4,5-dichloroimidazole (compound no. 1.2)

At room temperature (about 20° C.), 4.9 g of 4-(6-chloro-2-pyridinyloxy)phenol in 40 ml of anhydrous dimethylformamide is dripped into 0.6 g of 100% strength sodium hydride in 20 ml of anhydrous dimethylformamide. The mixture is subsequently stirred for 30 minutes at 50° C., and then 4.2 g of 1-chloromethyl-4,5-dichloroimidazole in 20 ml of anhydrous dimethylformamide is dripped in at room temperature. This mixture is stirred for 2 hours at 60° C. and overnight at room temperature. It is then stirred into 200 ml of ice water and the solution is extracted three times with methyl tert-butyl ether. The organic phase is washed with 5% strength sodium hydroxide solution and water, and dried, and the solvent is evaporated off under reduced pressure. The crude product obtained is recrystallized from toluene. There is obtained 6.6 g of 1-[4-(6-chloro-2-pyridinyloxy)phenoxymethyl]-4,5-dichloroimidazole; m.p.: 94°–98° C.

EXAMPLE 2

1[4-(3,6-Dimethyl-2-pyrazinyloxy)-phenoxymethyl]-4,5-dichloroimidazole (compound no. 1.13)

At room temperature (about 20° C.), 7.8 g of 4-(3,6-dimethyl-2-pyrazinyloxy)-phenol in 20 ml of anhydrous dimethylformamide is dripped into 1.3 g of 80% strength sodium hydride in 30 ml of anhydrous dimethylformamide. The mixture is stirred for one hour at 70° C., and then 6.68 g of 1-chloromethyl-4,5-dichloroimidazole in 30 ml of anhydrous dimethylformamide is dripped in. The mixture is stirred for 8 hours at 70° C. and overnight at room temperature. It is then stirred into 200 ml of ethyl acetate, and this mixture is washed twice with water, four times with 5% strength sodium hydroxide solution and twice with saturated sodium chloride solution. The organic phase is dried over magnesium sulfate and the solvent is evaporated off under reduced pressure. The crude product obtained is crystallized with n-hexane. There is obtained 8.9 g of 1-[4-(3,6-dimethyl-2-pyrazinyloxy)-phenoxymethyl]-4,5-dichloroimidazole; m.p.: 84°–85° C.

Compounds Iaa to Iae listed in Tables 1 to 5 below may be prepared in accordance with these manufacturing instructions. The substitution position on the heteroaromatic is shown by a dot.

Compounds Iaa to Iae listed in Tables 1 to 5 without any physical data may be prepared from corresponding intermediates; their action is expected to be similar.

TABLE 1

(Iaa)

| Compound No. | A | $R^1$ | $R^3$ | $R^4 = R^5$ | Phys. data mp. [°C.] |
|---|---|---|---|---|---|
| 1.1 | 6-fluoro-2-pyridyl | H | H | Cl | 90–95 |
| 1.2 | 6-chloro-2-pyridyl | H | H | Cl | 94–98 |
| 1.3 | 6-bromo-2-pyridyl | H | H | Cl | 99–101 |
| 1.4 | 6-trifluoromethyl-2-pyridyl | H | H | Cl | 58–60 |
| 1.5 | 6-methyl-2-pyridyl | H | H | Cl | |
| 1.6 | 6-ethoxy-2-pyridyl | H | H | Cl | |
| 1.7 | 5-chloro-2-pyridyl | H | H | Cl | 94–97 |
| 1.8 | 6-cyclopropyl-3-cyano-2-pyridyl | H | H | Cl | 149–154 |
| 1.9 | 2-pyrimidinyl | H | H | Cl | 154–175 |

TABLE 1-continued (Iaa) Structure: A—O—[phenyl with R¹]—OCH₂—N(—C(R³)=N...)—C(R⁴)=C(R⁵)

| Compound No. | A | R¹ | R³ | R⁴ = R⁵ | Phys. data mp. [°C.] |
|---|---|---|---|---|---|
| 1.10 | 6-(trifluoromethyl)pyrimidin-2-yl | H | H | Cl | 92–98 |
| 1.11 | 4,6-dimethylpyrimidin-2-yl | H | H | Cl | 109–122 |
| 1.12 | pyrazin-2-yl | H | H | Cl | 79–90 |
| 1.13 | 3,6-dimethylpyrazin-2-yl | H | H | Cl | 84–85 |
| 1.14 | 3,5-dimethylpyrazin-2-yl | H | H | Cl | |
| 1.15 | 6-methoxypyridazin-3-yl | H | H | Cl | 117–124 |
| 1.16 | pyridin-2-yl | H | H | Cl | |
| 1.17 | pyridin-2-yl | H | H | CH₃ | |
| 1.18 | 6-fluoropyridin-2-yl | H | H | CH₃ | |
| 1.19 | 6-chloropyridin-2-yl | H | H | CH₃ | |
| 1.20 | 6-bromopyridin-2-yl | H | H | CH₃ | |

TABLE 1-continued (Iaa) Structure: A—O—[phenyl with R¹]—OCH₂—N(R³)—N=C(R⁴)(R⁵)

| Compound No. | A | R¹ | R³ | R⁴ = R⁵ | Phys. data mp. [°C.] |
|---|---|---|---|---|---|
| 1.21 | 6-(trifluoromethyl)pyridin-2-yl | H | H | CH₃ | |
| 1.22 | 6-methylpyridin-2-yl | H | H | CH₃ | |
| 1.23 | 6-ethoxypyridin-2-yl | H | H | CH₃ | |
| 1.24 | 5-chloropyridin-2-yl | H | H | CH₃ | |
| 1.25 | 6-cyclopropyl-3-cyanopyridin-2-yl | H | H | CH₃ | |
| 1.26 | pyrimidin-2-yl | H | H | CH₃ | |
| 1.27 | 4-(trifluoromethyl)pyrimidin-2-yl | H | H | CH₃ | |
| 1.28 | 4-chloropyrimidin-2-yl | H | H | CH₃ | |
| 1.29 | pyrazin-2-yl | H | H | CH₃ | |
| 1.30 | 3,6-dimethylpyrazin-2-yl | H | H | CH₃ | |
| 1.31 | 3,5-dimethylpyrazin-2-yl | H | H | CH₃ | |

TABLE 1-continued (Iaa) structure: A—O—[phenyl with R¹]—OCH₂—N(R³)—C(=N)—C(R⁴)=C(R⁵)... (pyrimidinyl-type ring)

| Compound No. | A | R¹ | R³ | R⁴ = R⁵ | Phys. data mp. [°C.] |
|---|---|---|---|---|---|
| 1.32 | 6-methoxy-pyridazin-3-yl (CH₃O-pyridazine) | H | H | CH₃ | |
| 1.33 | pyridin-2-yl | H | H | H | |
| 1.34 | 6-fluoropyridin-2-yl | H | H | H | |
| 1.35 | 6-chloropyridin-2-yl | H | H | H | |
| 1.36 | 6-bromopyridin-2-yl | H | H | H | |
| 1.37 | 6-trifluoromethylpyridin-2-yl | H | H | H | |
| 1.38 | 6-methylpyridin-2-yl | H | H | H | |
| 1.39 | 6-ethoxypyridin-2-yl | H | H | H | |
| 1.40 | 5-chloropyridin-2-yl | H | H | H | |
| 1.41 | 6-cyclopropyl-3-cyano-pyridin-2-yl | H | H | H | |
| 1.42 | pyrimidin-2-yl | H | H | H | |

TABLE 1-continued $$\text{A-O-}\underset{R^1}{\underset{|}{\text{C}_6\text{H}_3}}\text{-OCH}_2\text{-N}\underset{R^4}{\overset{R^3}{\underset{\|}{\text{C}=\text{N}}}}\underset{R^5}{\overset{}{\text{C}}}$$ (Iaa)

| Compound No. | A | R¹ | R³ | R⁴ = R⁵ | Phys. data mp. [°C.] |
|---|---|---|---|---|---|
| 1.43 | 4-(F₃C)-pyrimidin-2-yl | H | H | H | |
| 1.44 | 4-Cl-pyrimidin-2-yl | H | H | H | |
| 1.45 | pyrazin-2-yl | H | H | H | |
| 1.46 | 3,6-dimethylpyrazin-2-yl | H | H | H | |
| 1.47 | 3,5-dimethylpyrazin-2-yl | H | H | H | |
| 1.48 | 6-methoxypyridazin-3-yl | H | H | H | |
| 1.49 | 4,6-dichloropyrimidin-2-yl | H | H | Cl | |
| 1.50 | pyrimidin-5-yl | H | H | Cl | |
| 1.51 | 6-chloropyrimidin-4-yl | H | H | Cl | |

TABLE 2

(Iab) structure: A—O—[phenyl with R¹]—OCH₂—N(pyrazole with R⁶, R⁷, R⁸)

| Compound No. | A | R¹ | R⁶ | R⁷ | R⁸ | Phys. data |
|---|---|---|---|---|---|---|
| 2.1 | pyridin-2-yl | H | H | H | H | |
| 2.2 | 6-fluoropyridin-2-yl | H | H | H | H | |
| 2.3 | 6-chloropyridin-2-yl | H | H | H | H | |
| 2.4 | 6-bromopyridin-2-yl | H | H | H | H | |
| 2.5 | 6-trifluoromethylpyridin-2-yl | H | H | H | H | |
| 2.6 | 6-methylpyridin-2-yl | H | H | H | H | |
| 2.7 | 6-ethoxypyridin-2-yl | H | H | H | H | |
| 2.8 | 5-chloropyridin-2-yl | H | H | H | H | |
| 2.9 | 6-cyclopropyl-3-cyanopyridin-2-yl | H | H | H | H | |
| 2.10 | pyrimidin-2-yl | H | H | H | H | |
| 2.11 | 4-trifluoromethylpyrimidin-2-yl | H | H | H | H | |
| 2.12 | 4-chloropyrimidin-2-yl | H | H | H | H | |
| 2.13 | pyrazin-2-yl | H | H | H | H | |
| 2.14 | 3,5-dimethylpyrazin-2-yl | H | H | H | H | |
| 2.15 | 3,6-dimethylpyrazin-2-yl | H | H | H | H | |
| 2.16 | 6-methoxypyridazin-3-yl | H | H | H | H | |
| 2.17 | 4,6-dichloropyrimidin-2-yl | H | H | H | H | |
| 2.18 | pyrimidin-5-yl | H | H | H | H | |
| 2.19 | 6-chloropyrimidin-4-yl | H | H | H | H | |

TABLE 3
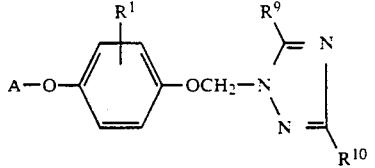
(Iac)
| Compound No. | A | R¹ | R⁹ = R₁₀ | Phys. data mp. [°C.] |
|---|---|---|---|---|
| 3.1 | 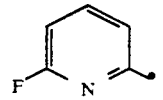 | H | H | 85–92 |
| 3.2 | 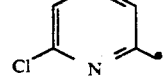 | H | H | 85–93 |
| 3.3 | 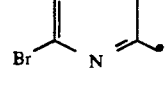 | H | H | 103–106 |
| 3.4 | 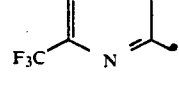 | H | H | 128–130 |
| 3.5 | 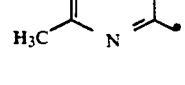 | H | H | 92–95 |
| 3.6 | 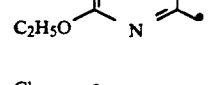 | H | H | 83–85 |
| 3.7 | 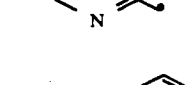 | H | H | |
| 3.8 | 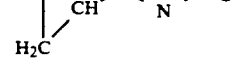 | H | H | 98–100 |
| 3.9 | 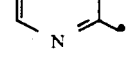 | H | H | 90–94 |
| 3.10 | 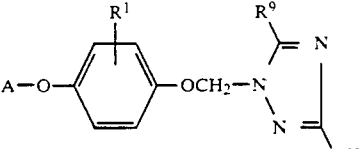 | H | H | 160–163 |
| 3.11 | 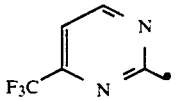 | H | H | |
| 3.12 | 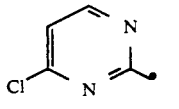 | H | H | |
| 3.13 | 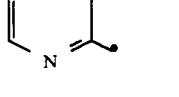 | H | H | 88–94 |
| 3.14 | 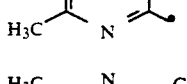 | H | H | |
| 3.15 | 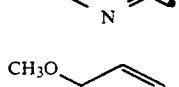 | H | H | 84–88 |
| 3.16 | 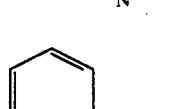 | H | H | |
| 3.17 |  | H | CH₃ | |
| 3.18 | 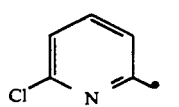 | H | CH₃ | |
| 3.19 | 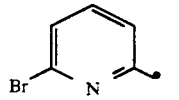 | H | CH₃ | |
| 3.20 | 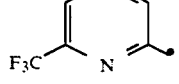 | H | CH₃ | |
| 3.21 |  | H | CH₃ | |

TABLE 3-continued (Iac)

A—O—[phenyl with R¹]—OCH₂—N(R⁹)—N=C(R¹⁰) (hydrazone structure)

| Compound No. | A | R¹ | R⁹ = R¹⁰ | Phys. data mp. [°C.] |
|---|---|---|---|---|
| 3.22 | 6-methyl-pyridin-2-yl | H | CH₃ | |
| 3.23 | 6-ethoxy-pyridin-2-yl | H | CH₃ | |
| 3.24 | 5-chloro-pyridin-2-yl | H | CH₃ | |
| 3.25 | 6-cyclopropyl-3-cyano-pyridin-2-yl | H | CH₃ | |
| 3.26 | pyrimidin-2-yl | H | CH₃ | |
| 3.27 | 4-trifluoromethyl-pyrimidin-2-yl | H | CH₃ | |
| 3.28 | 4-chloro-pyrimidin-2-yl | H | CH₃ | |
| 3.29 | pyrazin-2-yl | H | CH₃ | |
| 3.30 | 3,6-dimethyl-pyrazin-2-yl | H | CH₃ | |
| 3.31 | 3,6-dimethyl-pyrazin-2-yl (isomer) | H | CH₃ | |
| 3.32 | 6-methoxy-pyridazin-3-yl | H | CH₃ | |
| 3.33 | 4,6-dichloro-pyrimidin-2-yl | H | H | |
| 3.34 | 4,6-dichloro-pyrimidin-2-yl | H | CH₃ | |
| 3.35 | pyrimidin-5-yl | H | H | |
| 3.36 | pyrimidin-5-yl | H | CH₃ | |
| 3.37 | 6-chloro-pyrimidin-4-yl | H | H | |
| 3.38 | 6-chloro-pyrimidin-4-yl | H | CH₃ | |

TABLE 4

(Iad)

A—O—[phenyl with R¹]—OCH₂—N(indazol-1-yl with R¹¹)

| Compound No. | A | R¹ | R¹¹ | Phys. data |
|---|---|---|---|---|

TABLE 4-continued $$\text{(Iad)}$$

A—O—[phenyl with R¹]—OCH₂—N(N=)—[indazole with R¹¹]

| Compound No. | A | R¹ | R⁹ = R¹⁰ | Phys. data |
|---|---|---|---|---|
| 4.1 | pyridin-2-yl | H | H | |
| 4.2 | 6-fluoropyridin-2-yl | H | H | |
| 4.3 | 6-chloropyridin-2-yl | H | H | |
| 4.4 | 6-bromopyridin-2-yl | H | H | |
| 4.5 | 6-trifluoromethylpyridin-2-yl | H | H | |
| 4.6 | 6-methylpyridin-2-yl | H | H | |
| 4.7 | 6-ethoxypyridin-2-yl | H | H | |
| 4.8 | cyclopropyl-fused cyanopyridin-2-yl | H | H | |
| 4.9 | 5-chloropyridin-2-yl | H | H | |
| 4.10 | pyrimidin-2-yl | H | H | |
| 4.11 | 4-trifluoromethylpyrimidin-2-yl | H | H | |
| 4.12 | 4-chloropyrimidin-2-yl | H | H | |
| 4.13 | pyrazin-2-yl | H | H | |
| 4.14 | 3,5-dimethylpyrazin-2-yl | H | H | |
| 4.15 | 3,6-dimethylpyrazin-2-yl | H | H | |
| 4.16 | 6-methoxypyridazin-3-yl | H | H | |
| 4.17 | 4,6-dichloropyrimidin-2-yl | H | H | |
| 4.18 | pyrimidin-5-yl | H | H | |
| 4.19 | 6-chloropyrimidin-4-yl | H | H | |

TABLE 5

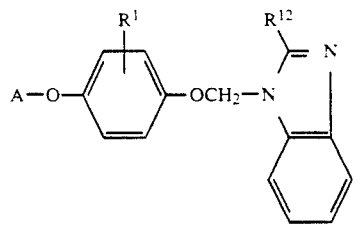

(Iae)

| Compound No. | A | $R^1$ | $R^{12}$ | Phys. data |
|---|---|---|---|---|
| 5.1 | 2-pyridyl | H | H | |
| 5.2 | 6-fluoro-2-pyridyl | H | H | |
| 5.3 | 6-chloro-2-pyridyl | H | H | |
| 5.4 | 6-bromo-2-pyridyl | H | H | |
| 5.5 | 6-trifluoromethyl-2-pyridyl | H | H | |
| 5.6 | 6-methyl-2-pyridyl | H | H | |
| 5.7 | 6-ethoxy-2-pyridyl | H | H | |
| 5.8 | 6-cyclopropyl-3-cyano-2-pyridyl | H | H | |
| 5.9 | 5-chloro-2-pyridyl | H | H | |
| 5.10 | 2-pyrimidinyl | H | H | |
| 5.11 | 4-trifluoromethyl-2-pyrimidinyl | H | H | |

TABLE 5-continued

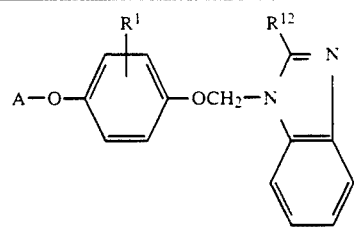

(Iae)

| Compound No. | A | $R^1$ | $R^{12}$ | Phys. data |
|---|---|---|---|---|
| 5.12 | 4-chloro-2-pyrimidinyl | H | H | |
| 5.13 | 4,6-dichloro-2-pyrimidinyl | H | H | |
| 5.14 | 5-pyrimidinyl | H | H | |
| 5.16 | 6-chloro-4-pyrimidinyl | H | H | |
| 5.17 | 3,5-dimethyl-2-pyrazinyl | H | H | |
| 5.18 | 3,6-dimethyl-2-pyrazinyl | H | H | |
| 5.19 | 6-methoxy-3-pyridazinyl | H | H | |
| 5.20 | 2-pyridyl | H | CH$_3$ | |
| 5.21 | 6-fluoro-2-pyridyl | H | CH$_3$ | |
| 5.22 | 6-chloro-2-pyridyl | H | CH$_3$ | |

TABLE 5-continued (Iae) structure: A—O—[phenyl with R¹]—OCH₂—N=C(R¹²)—[2-substituted phenyl ring]

| Compound No. | A | R¹ | R¹² | Phys. data |
|---|---|---|---|---|
| 5.23 | 6-bromo-2-pyridinyl (Br-pyridine) | H | CH₃ | |
| 5.24 | 6-trifluoromethyl-2-pyridinyl (F₃C-pyridine) | H | CH₃ | |
| 5.25 | 6-methyl-2-pyridinyl (H₃C-pyridine) | H | CH₃ | |
| 5.26 | 6-ethoxy-2-pyridinyl (C₂H₅O-pyridine) | H | CH₃ | |
| 5.27 | 3-cyano-6-cyclopropyl-2-pyridinyl | H | CH₃ | |
| 5.28 | 5-chloro-2-pyridinyl | H | CH₃ | |
| 5.29 | 2-pyrimidinyl | H | H | |
| 5.30 | 4-trifluoromethyl-2-pyrimidinyl | H | H | |
| 5.31 | 4-chloro-2-pyrimidinyl | H | H | |
| 5.32 | 4,6-dichloro-2-pyrimidinyl | H | CH₃ | |
| 5.33 | pyrazinyl | H | CH₃ | |
| 5.34 | chloropyrimidinyl (Cl-substituted) | H | CH₃ | |
| 5.35 | pyrazinyl | H | CH₃ | |
| 5.36 | 3,5,6-trimethylpyrazinyl (H₃C, CH₃, CH₃) | H | CH₃ | |
| 5.37 | 3,6-dimethylpyrazinyl (H₃C, CH₃) | H | CH₃ | |
| 5.38 | 6-methoxy-3-pyridazinyl (CH₃O-pyridazine) | H | CH₃ | |

EXAMPLE 4

2-[4-(6-Chloro-2-pyridinyloxy)-phenoxymethyl]-5-bromothiophene (Compound no. 6.3)

3.5 g of 4-(6-chloro-2-pyridinyloxy)-phenol and 3.2 g of potassium carbonate are stirred for one hour at 60° C. in 100 ml of anhydrous dimethylformamide. Subsequently, 6.5 g of 5-bromo-2-chloromethylthiophene in 30 ml of anhydrous dimethylformamide is dripped in. The mixture is stirred for 6 hours at 80° C. and overnight at room temperature (about 20° C.). The mixture is then poured into 200 ml of ice water. The crude product which precipitates out is filtered off and recrystallized from n-hexane/ethyl acetate (4/1). There is obtained 3.1 g of 2-[4-(6-chloro-2-pyridinyloxy)-phenoxymethyl]-5-bromothiophene of m.p.: 78°–80° C.

EXAMPLE 5

5-[4-(6-Chloro-2-pyridinyloxy)-phenoxymethyl]-3-cyclopropylisoxazole (Compound no. 6.22)

At room temperature (about 20° C.), 11.1 g of 4-(6-chloro-2-pyridinyloxy)phenol in 100 ml of anhydrous dimethylformamide is dripped into 1.3 g of 100% strength sodium hydride in 40 ml of anhydrous dimethylformamide. To complete the exothermic reaction (evolution of hydrogen) the mixture is stirred for 30 minutes at 50° C. At room temperature, 7.9 g of 5-chloromethyl-3-cyclopropylisoxazole in 30 ml of anhydrous dimethylformamide is then dripped in. The mixture is stirred for 2 hours at 60° C. and overnight at room temperature. It is then poured into 200 ml of ice water and the solution is extracted with methyl tert-butyl ether. The organic phase is then washed with sodium hydroxide solution, water and saturated sodium chloride solution. After drying over sodium sulfate, the solvent is evaporated under reduced pressure. The crude product is recrystallized from methanol. There is obtained 13.5 g of 5-[4-(6-chloro-2-pyridinyloxy)-phenoxymethyl]3-cyclopropylisoxazole of m.p.: 128°-130° C.

EXAMPLE 6

5-[4-(6-Chloro-2-pyridinyloxy)-phenoxymethyl]-2-ethoxy-1,3,4-thiadiazole (Compound no. 6.79)

At room temperature (about 20° C.), 4.9 g of 4-(6-chloro-2-pyridinyloxy)phenol in 40 ml of anhydrous dimethylformamide is dripped into 0.6 g of 100% strength sodium hydride in 20 ml of anhydrous dimethylformamide. To complete the exothermic reaction (evolution of hydrogen) the mixture is stirred for 30 minutes at 50° C. Subsequently, 4 g of 5-chloromethyl-2-ethoxy-1,3,4-thiadiazole in 20 ml of anhydrous dimethylformamide is dripped in and the mixture is stirred for 2 hours at 60° C. and overnight at room temperature. The mixture is then poured into 200 ml of ice water. The crude product which crystallizes out is filtered off and recrystallized from isopropanol. There is obtained 5.4 g of 5-[4-(6-chloro-2-pyridinyloxy)-phenoxymethyl]-2-ethoxy-1,3,4-thiadiazole of m.p.: 92° C.-94° C.

Compounds Ib listed in Table 6 below may be prepared in accordance with these manufacturing instructions. The substitution positions on the heteroaromatic are shown by a dot.

Compounds I in Table 6 below without any physical data may be prepared from corresponding intermediates; their action is expected to be similar.

TABLE 6

(Ib) $A-O-C_6H_3(R^1)-OCH(R^2)-Q_b$

| Compound No. | A | $R^1$ | $R^2$ | $Q_b$ | Phys. data/mp. [°C.] $^1$H-NMR in CDCl$_3$ δ [ppm] |
|---|---|---|---|---|---|
| 6.1 | 2-pyridinyl | H | H | 5-bromo-2-thienyl | |
| 6.2 | 6-fluoro-2-pyridinyl | H | H | 5-bromo-2-thienyl | 74-76 |
| 6.3 | 6-chloro-2-pyridinyl | H | H | 5-bromo-2-thienyl | 78-80 |
| 6.4 | 6-bromo-2-pyridinyl | H | H | 5-bromo-2-thienyl | 71-73 |
| 6.5 | 6-trifluoromethyl-2-pyridinyl | H | H | 5-bromo-2-thienyl | 70-72 |
| 6.6 | 6-methyl-2-pyridinyl | H | H | 5-bromo-2-thienyl | |
| 6.7 | 6-ethoxy-2-pyridinyl | H | H | 5-bromo-2-thienyl | |

TABLE 6-continued (Ib)

Structure: A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.8 | 6-cyclopropyl-3-cyano-pyridin-2-yl | H | H | 5-bromothien-2-yl | |
| 6.9 | 5-chloropyridin-2-yl | H | H | 5-bromothien-2-yl | 98–100 |
| 6.10 | pyrimidin-2-yl | H | H | 5-bromothien-2-yl | 103–106 |
| 6.11 | 4-trifluoromethylpyrimidin-2-yl | H | H | 5-bromothien-2-yl | |
| 6.12 | 4-chloropyrimidin-2-yl | H | H | 5-bromothien-2-yl | |
| 6.13 | 4,6-dimethylpyrimidin-2-yl | H | H | 5-bromothien-2-yl | |
| 6.14 | pyrimidin-5-yl | H | H | 5-bromothien-2-yl | 86–89 |
| 6.15 | 6-chloropyrimidin-4-yl | H | H | 5-bromothien-2-yl | |
| 6.16 | pyrazin-2-yl | H | H | 5-bromothien-2-yl | 120–124 |
| 6.17 | 3,6-dimethylpyrazin-2-yl | H | H | 5-bromothien-2-yl | 101–102 |

TABLE 6-continued (Ib)

$$A{-}O{-}\underset{\underset{OCH{-}Q_b}{|}}{\overset{\overset{R^1}{|}}{C_6H_3}}{-}R^2$$

| Compound No. | A | R¹ | R² | Q_b | Phys. data/mp. [°C.] ¹H-NMR in CDCl₃ δ [ppm] |
|---|---|---|---|---|---|
| 6.18 | 3,6-dimethylpyrazin-2-yl | H | H | 5-bromothiophen-2-yl | 91–93 |
| 6.19 | 6-methoxypyridazin-3-yl | H | H | 5-bromothiophen-2-yl | |
| 6.20 | pyridin-2-yl | H | H | 3-cyclopropylisoxazol-5-yl | 68–72 |
| 6.21 | 6-fluoropyridin-2-yl | H | H | 3-cyclopropylisoxazol-5-yl | 99–106 |
| 6.22 | 6-chloropyridin-2-yl | H | H | 3-cyclopropylisoxazol-5-yl | 128–130 |
| 6.23 | 6-bromopyridin-2-yl | H | H | 3-cyclopropylisoxazol-5-yl | 127–129 |
| 6.24 | 6-trifluoromethylpyridin-2-yl | H | H | 3-cyclopropylisoxazol-5-yl | 134–137 |
| 6.25 | 6-methylpyridin-2-yl | H | H | 3-cyclopropylisoxazol-5-yl | 97–101 |
| 6.26 | 6-ethoxypyrazin-2-yl | H | H | 3-cyclopropylisoxazol-5-yl | |
| 6.27 | 6-cyclopropyl-3-cyanopyridin-2-yl | H | H | 3-cyclopropylisoxazol-5-yl | 140–145 |

TABLE 6-continued (Ib)

structure: A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.28 | 5-chloro-pyridin-2-yl | H | H | 5-(cyclopropyl-CH)-isoxazol-3-yl | 116–118 |
| 6.29 | pyrimidin-2-yl | H | H | 5-(cyclopropyl-CH)-isoxazol-3-yl | 119–122 |
| 6.30 | 4-CF₃-pyrimidin-2-yl | H | H | 5-(cyclopropyl-CH)-isoxazol-3-yl | 175–180 |
| 6.31 | 4-Cl-pyrimidin-2-yl | H | H | 5-(cyclopropyl-CH)-isoxazol-3-yl | — |
| 6.32 | 4,6-dimethyl-pyrimidin-2-yl | H | H | 5-(cyclopropyl-CH)-isoxazol-3-yl | 81–85 |
| 6.33 | pyrimidin-5-yl | H | H | 5-(cyclopropyl-CH)-isoxazol-3-yl | 83–86 |
| 6.34 | 4-Cl-pyrimidin-6-yl | H | H | 5-(cyclopropyl-CH)-isoxazol-3-yl | 83–86 |
| 6.35 | pyrazin-2-yl | H | H | 5-(cyclopropyl-CH)-isoxazol-3-yl | 113–116 |
| 6.36 | 3,6-dimethyl-pyrazin-2-yl | H | H | 5-(cyclopropyl-CH)-isoxazol-3-yl | 94–95 |
| 6.37 | 3,5-dimethyl-pyrazin-2-yl | H | H | 5-(cyclopropyl-CH)-isoxazol-3-yl | 94–95 |

TABLE 6-continued
(Ib)
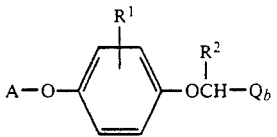
| Compound No. | A | R¹ | R² | $Q_b$ | Phys. data/mp. [°C.] ¹H-NMR in CDCl₃ δ [ppm] |
|---|---|---|---|---|---|
| 6.38 | 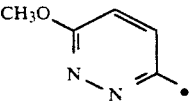 | H | H | 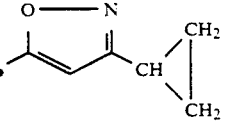 | 129–140 |
| 6.39 | 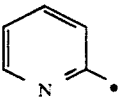 | H | H | 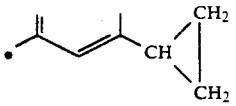 | |
| 6.40 | 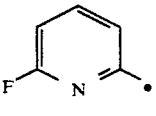 | H | H | 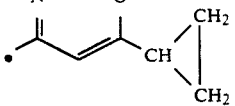 | |
| 6.41 | 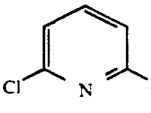 | H | H | 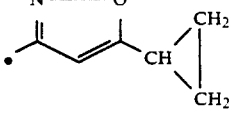 | |
| 6.42 | 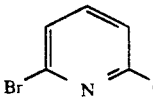 | H | H | 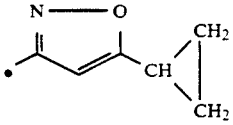 | |
| 6.43 | 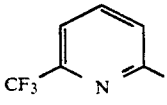 | H | H | 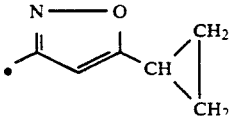 | |
| 6.44 | 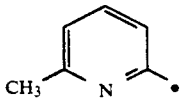 | H | H | 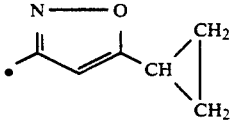 | |
| 6.45 | 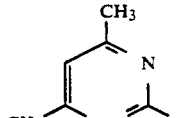 | H | H | 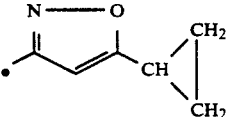 | |
| 6.46 | 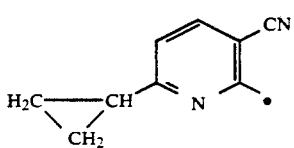 | H | H | 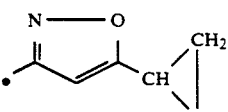 | |
| 6.47 | 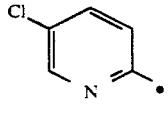 | H | H | 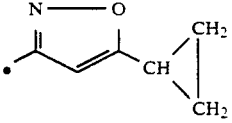 | |

TABLE 6-continued (Ib)

Structure: A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.48 | pyrimidin-2-yl | H | H | 3-(cyclopropyl)isoxazol-5-yl | |
| 6.49 | 4-(trifluoromethyl)pyrimidin-2-yl | H | H | 3-(cyclopropyl)isoxazol-5-yl | |
| 6.50 | 4-chloropyrimidin-2-yl | H | H | 3-(cyclopropyl)isoxazol-5-yl | |
| 6.51 | 4,6-dimethylpyrimidin-2-yl | H | H | 3-(cyclopropyl)isoxazol-5-yl | |
| 6.52 | pyrimidin-5-yl | H | H | 3-(cyclopropyl)isoxazol-5-yl | |
| 6.53 | 6-chloropyrimidin-4-yl | H | H | 3-(cyclopropyl)isoxazol-5-yl | |
| 6.54 | pyrazin-2-yl | H | H | 3-(cyclopropyl)isoxazol-5-yl | |
| 6.55 | 3,5-dimethylpyrazin-2-yl | H | H | 3-(cyclopropyl)isoxazol-5-yl | |
| 6.56 | 3,6-dimethylpyrazin-2-yl | H | H | 3-(cyclopropyl)isoxazol-5-yl | |
| 6.57 | 6-methoxypyridazin-3-yl | H | H | 3-(cyclopropyl)isoxazol-5-yl | |

TABLE 6-continued (Ib)

Structure: A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.58 | 2-pyridyl | H | H | N=N / cyclopropyl oxadiazole | |
| 6.59 | 6-fluoro-2-pyridyl | H | H | N=N / cyclopropyl oxadiazole | 80–84 |
| 6.60 | 6-chloro-2-pyridyl | H | H | N=N / cyclopropyl oxadiazole | 200 MHz: 2.15–2.30 (m), 5.23 (s), 7.01–7.21 (m). |
| 6.61 | 6-bromo-2-pyridyl | H | H | N=N / cyclopropyl oxadiazole | 250 NHz: 1.08–1.24 (m), 2.12–2.25 (m), 5.20 (s). |
| 6.62 | 6-trifluoromethyl-2-pyridyl | H | H | N=N / cyclopropyl oxadiazole | 250 MHz: 1.15–1.22 (m), 2.13–2.25 (m), 5.19 (s). |
| 6.63 | 6-methyl-2-pyridyl | H | H | N=N / cyclopropyl oxadiazole | |
| 6.64 | 3-cyclopropyl-isoxazol-5-yl | H | H | N=N / cyclopropyl oxadiazole | |
| 6.65 | 6-cyclopropyl-3-cyano-2-pyridyl | H | H | N=N / cyclopropyl oxadiazole | |
| 6.66 | 5-chloro-2-pyridyl | H | H | N=N / cyclopropyl oxadiazole | |
| 6.67 | 2-pyrimidinyl | H | H | N=N / cyclopropyl oxadiazole | 300-MHz: 1.05–1.38 (m), 5.21 (s), 6.85 – 7.30 (m) |

TABLE 6-continued (Ib)

Structure: A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.68 | 4-CF₃-pyrimidin-2-yl | H | H | 2-(cyclopropyl-methylene)-1,3,4-oxadiazol-5-yl | |
| 6.69 | 4-Cl-pyrimidin-2-yl | H | H | 2-(cyclopropyl-methylene)-1,3,4-oxadiazol-5-yl | |
| 6.70 | 4,6-dimethyl-pyrimidin-2-yl | H | H | 2-(cyclopropyl-methylene)-1,3,4-oxadiazol-5-yl | 125–130 |
| 6.71 | pyrimidin-5-yl | H | H | 2-(cyclopropyl-methylene)-1,3,4-oxadiazol-5-yl | |
| 6.72 | 6-Cl-pyrimidin-4-yl | H | H | 2-(cyclopropyl-methylene)-1,3,4-oxadiazol-5-yl | |
| 6.73 | pyrazin-2-yl | H | H | 2-(cyclopropyl-methylene)-1,3,4-oxadiazol-5-yl | 51–57 |
| 6.74 | 3,5-dimethyl-pyrazin-2-yl | H | H | 2-(cyclopropyl-methylene)-1,3,4-oxadiazol-5-yl | 78–82 |
| 6.75 | 3,6-dimethyl-pyrazin-2-yl | H | H | 2-(cyclopropyl-methylene)-1,3,4-oxadiazol-5-yl | 125–128 |
| 6.76 | 3-methoxy-pyridazin-6-yl | H | H | 2-(cyclopropyl-methylene)-1,3,4-oxadiazol-5-yl | 47–52 |
| 6.77 | pyridin-2-yl | H | H | 2-(ethoxy)-1,3,4-thiadiazol-5-yl | 55–57 |

TABLE 6-continued (Ib)

Structure: A—O—[phenyl with R¹, R²]—OCH—Q_b

| Compound No. | A | R¹ | R² | Q_b | Phys. data/mp. [°C.] ¹H-NMR in CDCl₃ δ [ppm] |
|---|---|---|---|---|---|
| 6.78 | 6-fluoropyridin-2-yl | H | H | N=N / φ-C(S)-C-OC₂H₅ (thiadiazole) | 79–83 |
| 6.79 | 6-chloropyridin-2-yl | H | H | same | 92–94 |
| 6.80 | 6-bromopyridin-2-yl | H | H | same | 80–81 |
| 6.81 | 6-trifluoromethylpyridin-2-yl | H | H | same | 90–91 |
| 6.82 | 6-methylpyridin-2-yl | H | H | same | |
| 6.83 | 6-ethoxypyridin-2-yl | H | H | same | |
| 6.84 | 6-cyclopropyl-3-cyanopyridin-2-yl | H | H | same | 128–130 |
| 6.85 | 5-chloropyridin-2-yl | H | H | same | 93–95 |
| 6.86 | pyrimidin-2-yl | H | H | same | 92–93 |
| 6.87 | 4-trifluoromethylpyrimidin-2-yl | H | H | same | 105–107 |
| 6.88 | 4-chloropyrimidin-2-yl | H | H | same | 121–123 |

TABLE 6-continued (Ib)

A—O—[phenyl with R¹]—OCH(R²)—Q_b

| Compound No. | A | R¹ | R² | Q_b | Phys. data/mp. [°C.] ¹H-NMR in CDCl₃ δ [ppm] |
|---|---|---|---|---|---|
| 6.89 | 4,6-dimethylpyrimidin-2-yl (CH₃, CH₃) | H | H | 2-phenyl-5-ethoxy-1,3,4-thiadiazole | 97–98 |
| 6.90 | pyrimidin-4-yl | H | H | 2-phenyl-5-ethoxy-1,3,4-thiadiazole | 86–88 |
| 6.91 | 6-chloropyrimidin-4-yl | H | H | 2-phenyl-5-ethoxy-1,3,4-thiadiazole | |
| 6.92 | pyrazin-2-yl | H | H | 2-phenyl-5-ethoxy-1,3,4-thiadiazole | 86–87 |
| 6.93 | 3,5-dimethylpyrazin-2-yl | H | H | 2-phenyl-5-ethoxy-1,3,4-thiadiazole | 100–101 |
| 6.94 | 3,6-dimethylpyrazin-2-yl | H | H | 2-phenyl-5-ethoxy-1,3,4-thiadiazole | |
| 6.95 | 6-methoxypyridazin-3-yl | H | H | 2-phenyl-5-ethoxy-1,3,4-thiadiazole | |
| 6.96 | pyridin-2-yl | H | H | 3-phenyl-1-methyl-5-cyclopropyl-pyrazole | |
| 6.97 | 6-fluoropyridin-2-yl | H | H | 3-phenyl-1-methyl-5-cyclopropyl-pyrazole | 66–69 |
| 6.98 | 6-chloropyridin-2-yl | H | H | 3-phenyl-1-methyl-5-cyclopropyl-pyrazole | 89–90 |

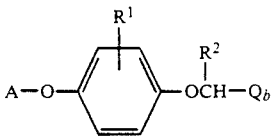

TABLE 6-continued
(Ib)
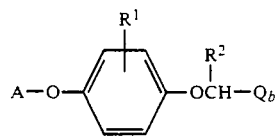
| Compound No. | A | R¹ | R² | $Q_b$ | Phys. data/mp. [°C.] ¹H-NMR in CDCl₃ δ [ppm] |
|---|---|---|---|---|---|
| 6.107 | 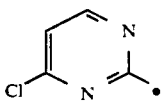 | H | H | 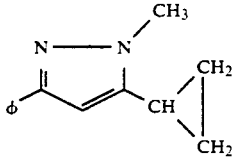 | |
| 6.108 | 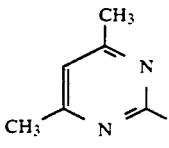 | H | H | 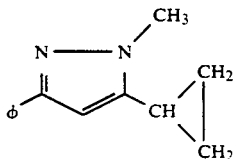 | |
| 6.109 | 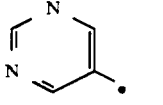 | H | H | 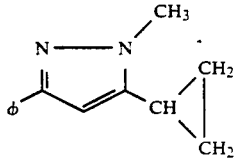 | 37–38 |
| 6.110 | 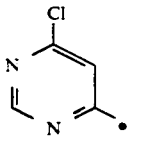 | H | H | 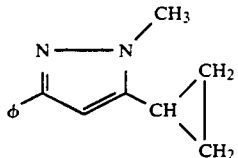 | |
| 6.111 | 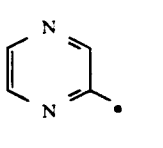 | H | H | 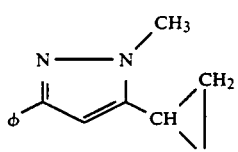 | 88–89 |
| 6.112 | 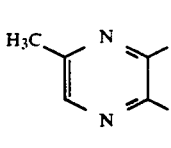 | H | H | 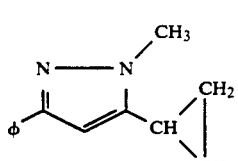 | 82–83 |
| 6.113 | 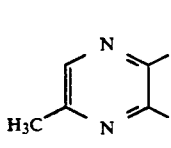 | H | H | 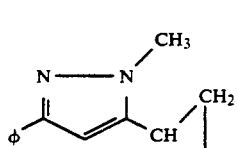 | |
| 6.114 | 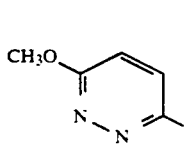 | H | H | 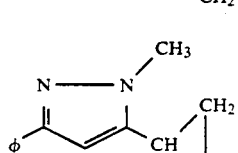 | |

TABLE 6-continued (Ib)

| Compound No. | A | R¹ | R² | $Q_b$ | Phys. data/mp. [°C.] ¹H-NMR in CDCl₃ δ [ppm] |
|---|---|---|---|---|---|
| 6.115 | 2-pyridyl | H | H | N=N / S-C(=)-CH(CH₂CH₂) cyclopropyl | 72 |
| 6.116 | 6-fluoro-2-pyridyl | H | H | same | 92–94 |
| 6.117 | 6-chloro-2-pyridyl | H | H | same | 76–78 |
| 6.118 | 6-bromo-2-pyridyl | H | H | same | 69–71 |
| 6.119 | 6-CF₃-2-pyridyl | H | H | same | 80–82 |
| 6.120 | 6-methyl-2-pyridyl | H | H | same | |
| 6.121 | 2-(cyclopropyl-CH)thiazolyl | H | H | same | |
| 6.122 | 4-methoxy-2-pyrimidinyl | H | H | same | 136–138 |
| 6.123 | 5-chloro-2-pyridyl | H | H | same | 90–91 |
| 6.124 | 2-pyrimidinyl | H | H | same | 93–94 |

TABLE 6-continued (Ib)

| Compound No. | A | R¹ | R² | Q_b | Phys. data/mp. [°C.] ¹H-NMR in CDCl₃ δ [ppm] |
|---|---|---|---|---|---|
| 6.125 | 4-CF₃-pyrimidin-2-yl | H | H | 5-(cyclopropyl-CH)-1,3,4-thiadiazol-2-yl | 130–134 |
| 6.126 | 4-Cl-pyrimidin-2-yl | H | H | 5-(cyclopropyl-CH)-1,3,4-thiadiazol-2-yl | 97–99 |
| 6.127 | 4,6-dimethylpyrimidin-2-yl | H | H | 5-(cyclopropyl-CH)-1,3,4-thiadiazol-2-yl | 110–111 |
| 6.128 | pyrimidin-5-yl | H | H | 5-(cyclopropyl-CH)-1,3,4-thiadiazol-2-yl | 74–76 |
| 6.129 | 6-Cl-pyrimidin-4-yl | H | H | 5-(cyclopropyl-CH)-1,3,4-thiadiazol-2-yl | — |
| 6.130 | pyrazin-2-yl | H | H | 5-(cyclopropyl-CH)-1,3,4-thiadiazol-2-yl | 99–100 |
| 6.131 | 3,5-dimethylpyrazin-2-yl | H | H | 5-(cyclopropyl-CH)-1,3,4-thiadiazol-2-yl | 107–109 |
| 6.132 | 3,6-dimethylpyrazin-2-yl | H | H | 5-(cyclopropyl-CH)-1,3,4-thiadiazol-2-yl | 86–87 |
| 6.133 | 6-methoxypyridazin-3-yl | H | H | 5-(cyclopropyl-CH)-1,3,4-thiadiazol-2-yl | — |
| 6.134 | pyridin-2-yl | H | H | 5-(cyclopropyl-CH)-1,3,4-thiadiazol-2-yl | — |

TABLE 6-continued
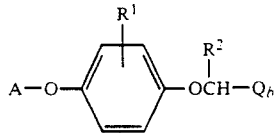
(Ib)
| Compound No. | A | R¹ | R² | $Q_b$ | Phys. data/mp. [°C.] ¹H-NMR in CDCl₃ δ [ppm] |
|---|---|---|---|---|---|
| 6.135 | 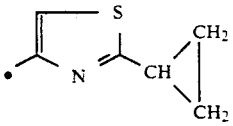 | H | H | 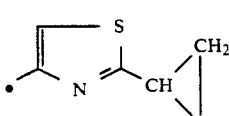 | 68-70 |
| 6.136 | 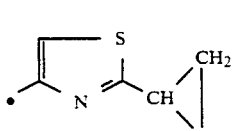 | H | H | | 63-67 |
| 6.137 | 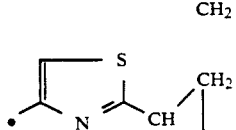 | H | H | | 52-54 |
| 6.138 | 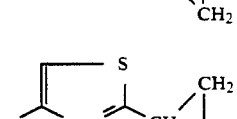 | H | H | | 63-65 |
| 6.139 | 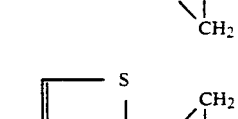 | H | H | | 73-75 |
| 6.140 | 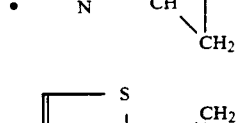 | H | H | | 61-66 |
| 6.141 | 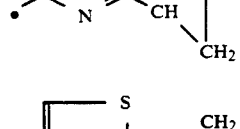 | H | H | | |
| 6.142 | | H | H | | |
| 6.143 | 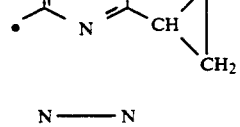 | H | H | | 85-87 |
Use Examples
In the following examples, the action of compounds according to the invention, or agents containing them, was compared with that of the following prior art compounds:

A 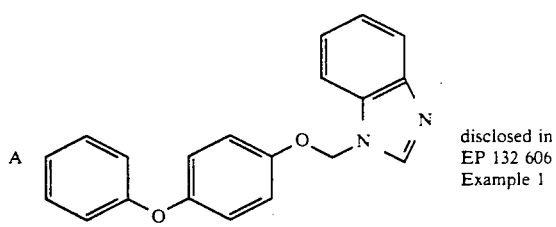

disclosed in
EP 132 606
Example 1

B 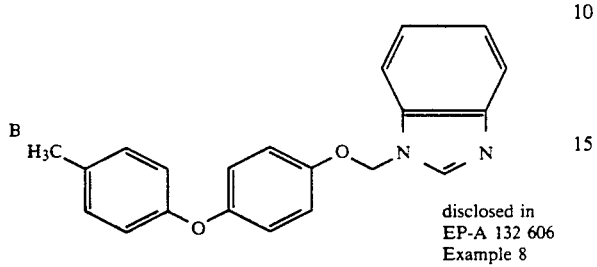

disclosed in
EP-A 132 606
Example 8

The purity of the comparative agents was the same as that of the inventive compounds and was at least 90 to 95%. The concentrations at which the compounds exhibit 100% kill or inhibition are the minimum concentrations. At least two experiments were run for each concentration.

EXAMPLE A

*Dysdercus intermedius* (cotton stainer); ovicidal action

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel.

The eggs were then dipped for about 5 seconds into aqueous formulations of the active ingredients and excess liquid was allowed to drip off onto filter paper, care being taken to prevent the eggs coming into contact with the paper.

The markers were placed (adhesive tape up) in plastic pallets. Half a roll of absorbent cotton was moistened with water and placed in each beaker to prevent drying out, and the pallets were covered with a glass plate.

Assessment took place after about 8 days (after the larvae in the control batch had hatched). Hatch inhibition was assessed in %.

In this experiment, compounds 1.2, 1.3, 6.60 and 6.79, applied at a concentration of 400 ppm and less, achieved 80 to 100% hatch inhibition, whereas comparative agents A to C did not inhibit hatching at all at an application rate of 1,000 ppm.

EXAMPLE 8

*Prodenia litura* (Egyptian cotton worm); breeding experiment

Breeding took place on a culture medium made up of 515 g of cornflour, 130 g of wheat germ, 137 g of brewer's yeast, 18 g of ascorbic acid, 10 g of cellulose powder, 5 g of Nipagin, 5 g of sorbic acid, 20 g of Wessons salt, 2 g of vitamins (Lutavit blend), 5 ml of chloramphenicol (0.1% strength in ethanol), 80 g of agar, and 3,100 of water. 100 g of this medium was introduced into 250 ml beakers, and the aqueous active ingredient formulations were carefully admixed.

After the vessels had cooled, 5 caterpillars in the fourth larval stage were introduced into each vessel, and the vessels were stored at 23° C. The kill rate was assessed after the moths in the untreated control had hatched.

In this experiment, compounds 6.33 and 6.24 achieved a kill of 80 to 100% at a rate of 0.04 ppm. Comparative agents A, B and C had no effect at a rate of 1 ppm.

We claim:

1. A compound of the formula Ia or Ib

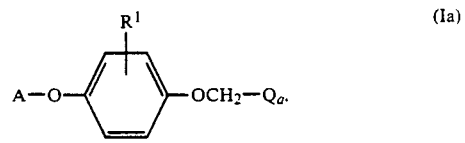 (Ia)

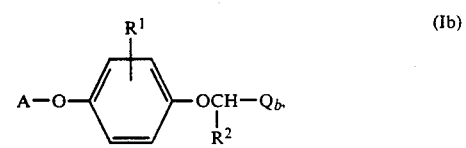 (Ib)

where A is

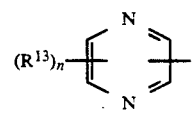

where the radicals $R^{13}$ are identical or different and are each hydrogen, halogen, $C_1$-$C_4$-alkyl, $C_1$-$C_3$-haloalkyl, $C_1$-$C_4$-alkoxy, $C_1$-$C_3$-haloalkoxy, $C_3$-$C_6$-cycloalkyl, cyano or nitro and n is from 1 to 4, $R^1$ is hydrogen, halogen or $C_1$-$C_3$-alkyl; $R^2$ is hydrogen or $C_1$-$C_4$-alkyl; $Q_a$ is an unsubstituted or substituted azole radical of the formulae IIa to IIe

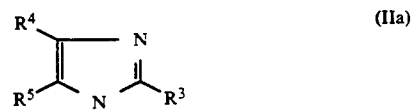 (IIa)

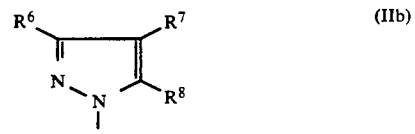 (IIb)

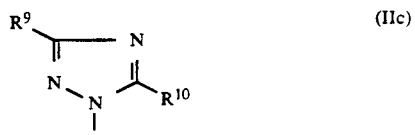 (IIc)

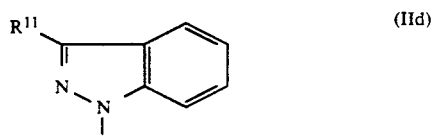 (IId)

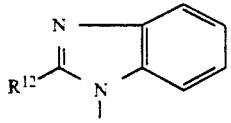

where $R^3$ to $R^{12}$ are hydrogen, halogen, $C_1-C_8$-alkyl, $C_1-C_4$-haloalkyl, $C_1-C_4$-alkoxy, $C_3-C_{10}$-cycloalkyl or are phenyl or naphthyl which is unsubstituted or mono- to trisubstituted by halogen, $C_1-C_8$-alkyl, $C_1-C_8$-alkoxy, $C_1-C_4$-haloalkyl or $C_1-C_3$-haloalkoxy, and $Q_b$ is a heteroaromatic radical selected from the group consisting of thiophen-2-yl; thiophen-3-yl; thiazol-2-yl; thiazol-4-yl; thiazol-5-yl; oxazol-2-yl; oxazol-4-yl; oxazol-5-yl; imidazol-2-yl; imidazol-4-yl; imidazol-5-yl; isothiazol-3-yl; isothiazol-4-yl; isothiazol-5-yl; pyrazol-3-yl; pyrazol-4-yl; isoxazol-3-yl; isoxazol-5-yl; 1,3,4-thiadiazol-2-yl; 1,3,4-oxadiazol-2-yl; 1,2,4-oxadiazol-3-yl; 1,3,4-triazol-2-yl; and 1,2,4-thiadiazol-3-yl and is unsubstituted or mono- or poly-substituted by halogen, $C_1-C_8$-alkyl, $C_2-C_8$-alkenyl, $C_1-C_4$-haloalkyl, $C_1-C_8$-alkoxy, $C_1-C_8$-alkylthio, $C_2-C_8$-alkoxyalkyl or $C_3-C_{10}$-cycloalkyl.

2. An insecticidal, arachnidicidal or nematodicidal composition comprising an insecticidally, arachnidicidally or nematodicidally effective amount of a compound of claim 1 and an inert carrier.

3. A process for combating pests selected from the group consisting of insects, arachnids, and nematodes, wherein the insects, arachnids, or nematodes, or the areas or spaces to be kept free from insects, arachnids, or nematodes, are treated with an insecticidally, arachnidicidally or nematodicidally effective amount of a compound of claim 1.

4. A compound of the formula Ia

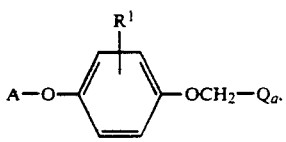

(Ia)

where A is

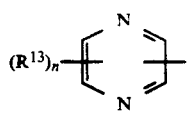

where the radicals $R^{13}$ are identical or different and are each hydrogen, halogen, $C_1-C_8$-alkyl, $C_1-C_4$-haloalkyl, $C_1-C_4$-alkoxy, $C_3-C_{10}$-cycloalkyl, or is phenyl or naphthyl which is unsubstituted or mono- to trisubstituted by halogen, $C_1-C_8$-alkyl, $C_1-C_8$-alkoxy, $C_1-C_4$-haloalkyl or $C_1-C_3$-haloalkoxy, $R^1$ is hydrogen, halogen or $C_1-C_3$-alkyl; and $Q_a$ is an unsubstituted or substituted azole radical of the formulae IIa to IIe

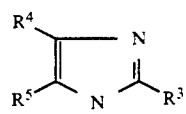

(IIa)

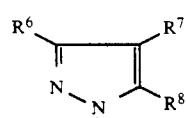

(IIb)

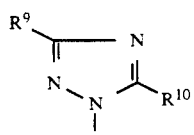

(IIc)

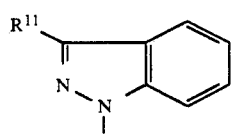

(IId)

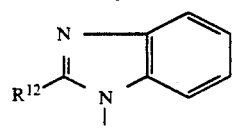

(IIe)

where $R^3$ to $R^{12}$ are hydrogen, halogen, $C_1-C_8$-alkyl, $C_1-C_4$-haloalkyl, $C_1-C_4$-alkoxy, $C_3-C_{10}$-cycloalkyl or are phenyl or naphthyl which is unsubstituted or mono- to trisubstituted by halogen, $C_1-C_8$-alkyl, $C_1-C_8$-alkoxy, $C_1-C_4$-haloalkyl or $C_1-C_3$-haloalkoxy.

5. An insecticidal, arachnidicidal or nematodicidal composition comprising an inert carrier and an insecticidally, arachnidicidally or nematodicidally effective amount of a compound of claim 4.

6. A compound of claim 4, wherein A is 3,6-dimethyl-2-pyrazinyl, $R^1$ is hydrogen, and $Q_a$ has the formula (IIa) wherein $R^3$ is hydrogen and $R^4$ and $R^5$ are chloro.

* * * * *